U S010244995B2

(12) United States Patent
Jang et al.

(10) Patent No.: US 10,244,995 B2
(45) Date of Patent: Apr. 2, 2019

(54) STORAGE UNIT AND MOBILE X-RAY IMAGING APPARATUS INCLUDING THE SAME

(71) Applicant: Samsung Electronics Co., Ltd., Gyeonggi-do (KR)

(72) Inventors: Ku-Il Jang, Yongin-si (KR); Jung Min Kim, Suwon-si (KR); Jae Won Nam, Yongin-si (KR); Seung Hwan Lee, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/657,035

(22) Filed: Jul. 21, 2017

(65) Prior Publication Data

US 2018/0020995 A1 Jan. 25, 2018

(30) Foreign Application Priority Data

Jul. 21, 2016 (KR) .................. 10-2016-0092487
Nov. 28, 2016 (KR) .................. 10-2016-0159608
Jun. 14, 2017 (KR) .................. 10-2017-0074939

(51) Int. Cl.
*A61B 6/00* (2006.01)
*A61B 6/10* (2006.01)

(52) U.S. Cl.
CPC ............ *A61B 6/102* (2013.01); *A61B 6/4405* (2013.01); *A61B 6/56* (2013.01); *A61B 6/4266* (2013.01); *A61B 6/4283* (2013.01)

(58) Field of Classification Search
CPC ......... A61B 6/4405; A61B 6/102; A61B 6/56; A61B 6/42; A61B 6/4266; A61B 6/4283
See application file for complete search history.

(56) References Cited

U.S. PATENT DOCUMENTS

| 2,149,040 | A | * | 2/1939 | Binder | .................. B64C 25/60 188/298 |
| 3,031,249 | A | * | 4/1962 | Koch | .................. A47B 88/493 312/334.12 |
| 5,138,160 | A | * | 8/1992 | Shimizu | .............. G03B 42/045 250/589 |
| 2012/0281817 | A1 | | 11/2012 | McBroom et al. | |

(Continued)

FOREIGN PATENT DOCUMENTS

| JP | 2006296676 A | * | 11/2006 | ............... A61B 6/00 |
| KR | 10-2016-0015139 A | | 2/2016 | |
| KR | 20160035510 A | * | 3/2016 | ........... A61B 6/4283 |

OTHER PUBLICATIONS

Communication from a foreign patent office in a foreign counterpart application, European Patent Office, "European Search Report," European Application No. EP 17 17 9606.3, dated Dec. 20, 2017, 7 pages.

(Continued)

*Primary Examiner* — Chih-Cheng Kao

(57) ABSTRACT

Disclosed herein is a mobile x-ray imaging apparatus having an improved structure to prevent breakage of or damage to an x-ray detector. One or more damping units are installed at base plates of one or more slots. The one or more damping units minimize an impact that may be applied to one or more x-ray detectors in a process of storing the one or more x-ray detector in the one or more slots.

20 Claims, 19 Drawing Sheets

(56) References Cited

U.S. PATENT DOCUMENTS

| | | | | |
|---|---|---|---|---|
| 2013/0064351 A1* | 3/2013 | Urbon | ............... | A61B 6/4283 |
| | | | | 378/98.5 |
| 2013/0134930 A1* | 5/2013 | Konkle | ............. | H02J 7/0027 |
| | | | | 320/108 |
| 2013/0301801 A1* | 11/2013 | Liu | ..................... | H05G 1/08 |
| | | | | 378/91 |
| 2016/0120489 A1* | 5/2016 | Yang | ................. | A61B 6/4283 |
| | | | | 378/62 |

OTHER PUBLICATIONS

Office Action dated Jun. 19, 2018 in connection with Korean Patent Application No. 10-2017-0074939.
Notice of Allowance dated Nov. 13, 2018 in connection with Korean Patent Application No. 10-2017-0074939, 3 pages.

* cited by examiner

STORAGE UNIT AND MOBILE X-RAY IMAGING APPARATUS INCLUDING THE SAME

CROSS-REFERENCE TO RELATED APPLICATION(S) AND CLAIM OF PRIORITY

The present application is related to Korean Patent Application Nos. 10-2016-0092487, 10-2016-0159608, and 10-2017-0074939 filed on Jul. 21, 2016, Nov. 28, 2016, and Jun. 14, 2017, respectively, in the Korean Intellectual Property Office, the disclosures of each is incorporated herein by reference.

TECHNICAL FIELD

The present disclosure relates to a storage unit and a mobile x-ray imaging apparatus including the same, and more particularly, to a storage unit and a mobile x-ray imaging apparatus including the same having an improved structure to prevent breakage of or damage to an x-ray detector.

BACKGROUND

An x-ray imaging apparatus is an apparatus using x-rays to obtain an image of an inside of an object. An x-ray imaging apparatus may irradiate an object with x-rays and detect x-rays that have passed through the object to form an image of an inside of the object with a non-invasive method. A medical x-ray imaging apparatus may be used in diagnosing an injury, a disease, or the like that cannot be diagnosed from outside.

A typical x-ray imaging apparatus has an x-ray source and an x-ray detector fixed within a predetermined space. Consequently, a patient has to move to an examination room in which an x-ray imaging apparatus is disposed to perform x-ray imaging.

However, because it is difficult to perform x-ray imaging using a typical x-ray imaging apparatus in a case of a patient with mobility difficulties, a mobile x-ray imaging apparatus capable of performing x-ray imaging regardless of location has been developed.

Because a mobile x-ray imaging apparatus has an x-ray source mounted at a movable main body and uses a portable x-ray detector, x-ray imaging may be performed by directly going to a patient with mobility difficulties.

One or more x-ray detectors may be stored in a mobile x-ray imaging apparatus. A considerable amount of impact may be applied to the one or more x-ray detectors during a process of storing the one or more x-ray detectors in the mobile x-ray imaging apparatus. As a result, breakage of or damage to the one or more x-ray detectors may occur.

SUMMARY

To address the above-discussed deficiencies, it is a primary object to provide a storage unit and a mobile x-ray imaging apparatus including the same having an improved structure to improve impact absorbing effect for an x-ray detector.

It is another aspect of the present disclosure to provide a storage unit and a mobile x-ray imaging apparatus including the same having an improved structure to prevent an x-ray detector from being accelerated due to gravity during a process of storing the x-ray detector in the mobile x-ray imaging apparatus.

It is still another aspect of the present disclosure to provide a storage unit and a mobile x-ray imaging apparatus including the same having an improved structure to improve success rate of docking an x-ray detector to a charging terminal.

It is yet another aspect of the present disclosure to provide a storage unit and a mobile x-ray imaging apparatus including the same having an improved structure for easily detaching an x-ray detector from a charging terminal.

According to the spirit of the present disclosure, since one or more damping units are installed in a storage unit of a mobile x-ray imaging apparatus, an impact that may be applied to the one or more x-ray detectors stored in the storage unit may be effectively prevented.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1A through 10, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1A:
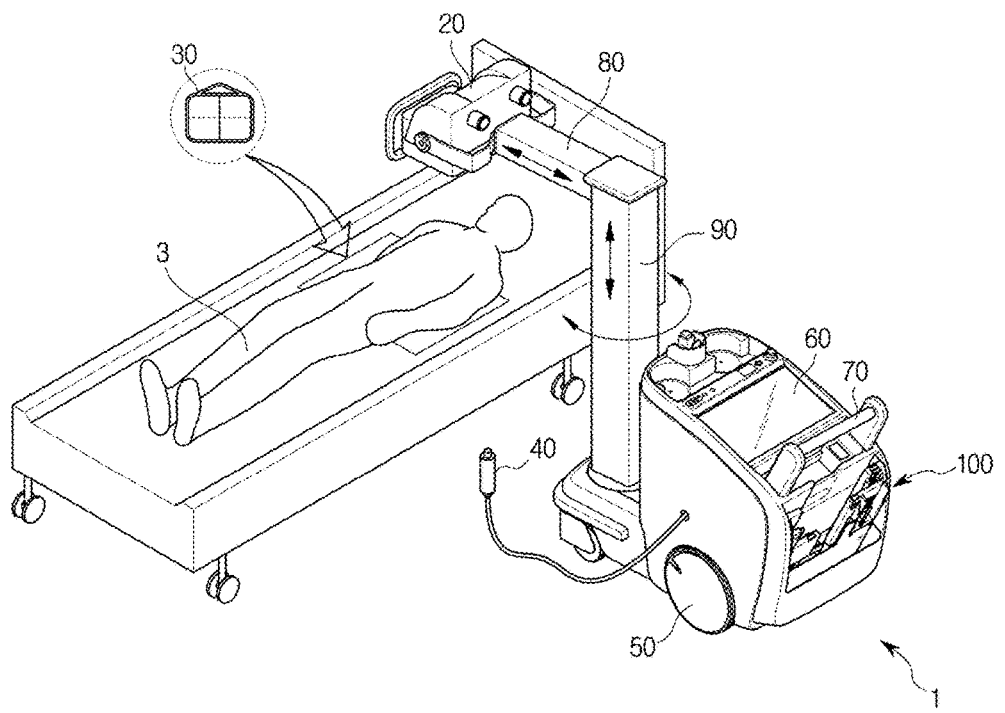
FIG. 1A illustrates a usage example of a mobile x-ray imaging apparatus according to an embodiment of the present disclosure.

FIG. 1A illustrates a usage example of a mobile x-ray imaging apparatus according to an embodiment of the present disclosure. Hereinafter, reference numeral "3" refers to an object to be x-rayed. Here, the object may be a living body of a human or an animal but is not limited thereto. The object may be anything of which an image of an inner structure thereof may be formed by a mobile x-ray imaging apparatus 1.

As illustrated in FIG. 1A, the mobile x-ray imaging apparatus 1 may include a main body 10. The main body 10 may be movable. A controller (not illustrated) may be provided in the main body 10. The controller may control an x-ray source 20 to control generation of x-rays. Also, the controller may receive an electrical signal from one or more x-ray detectors 30 and generate an x-ray image.

The mobile x-ray imaging apparatus 1 may further include a hand switch 40. The hand switch 40 may receive a command from a user and transmit the command to the controller. A command received by the hand switch 40 may include an x-ray radiation readying command or an x-ray radiating command. For example, a user may input the x-ray irradiation readying command through the hand switch 40 for image capturing by the mobile x-ray imaging apparatus 1. Also, when preparation for image capturing is finished, the user may input the x-ray radiating command through the hand switch 40 so that the x-ray source 20 radiates x-rays.

The mobile x-ray imaging apparatus 1 may further include a plurality of wheels 50 configured to give mobility to the main body 10.

The mobile x-ray imaging apparatus 1 may further include a display 60. The display 60 may display information on a patient, an x-ray image, and the like. The display 60 may be installed at the main body 10. The display 60 may include a touch screen function.

The mobile x-ray imaging apparatus 1 may further include a handle 70 provided at the main body 10. A user may grip the handle 70 and push or pull the main body 10.

The mobile x-ray imaging apparatus 1 may further include a support arm 80 and a support frame 90. The x-ray source 20 that will be described below may be mounted on the movable main body 10 by the support arm 80. The support arm 80 may be mounted on the support frame 90 to be rotatable in a vertical direction. The support frame 90 may be mounted at one side of the main body 10 to be rotatable in a horizontal direction. As a result, since the support arm 80 is rotatable and a tilt angle thereof may be changed, the x-ray source 20 may freely move.

The mobile x-ray imaging apparatus 1 may further include the x-ray source 20 configured to generate and radiate x-rays. As described above, the x-ray source 20 may be coupled to the support arm 80. The x-ray source 20 receives power and generates x-rays. Energy of x-rays may be controlled by a tube voltage, and intensity and dose of x-rays may be controlled by a tube current and x-ray exposure time.

The mobile x-ray imaging apparatus 1 may further include the one or more x-ray detectors 30 provided to detect x-rays radiated from the x-ray source 20. The one or more x-ray detectors 30 may have various sizes depending on an object for x-ray image capturing. The one or more x-ray detectors 30 may be wirelessly realized for convenience of use. The one or more x-ray detectors 30 may be stored in a storage unit 100 after capturing an x-ray image. Also, the one or more x-ray detectors 30 may be charged while being stored in the storage unit 100.

Each of the one or more x-ray detectors 30 may include a terminal 31 (see FIG. 7A) formed at one side thereof. Also, each of the one or more x-ray detectors 30 may further include a detector magnetic body 32 (see FIG. 7A). The detector magnetic body 32 may be provided near the terminal 31. Specifically, the detector magnetic body 32 may be provided at one side of each of the one or more x-ray detectors 30 to be adjacent to the terminal 31.

The mobile x-ray imaging apparatus 1 may further include the storage unit 100 provided to have the one or more x-ray detectors 30 stored therein. The storage unit 100 may be provided at the main body 10. The storage unit 100 will be described in detail below.

Figure 1B:
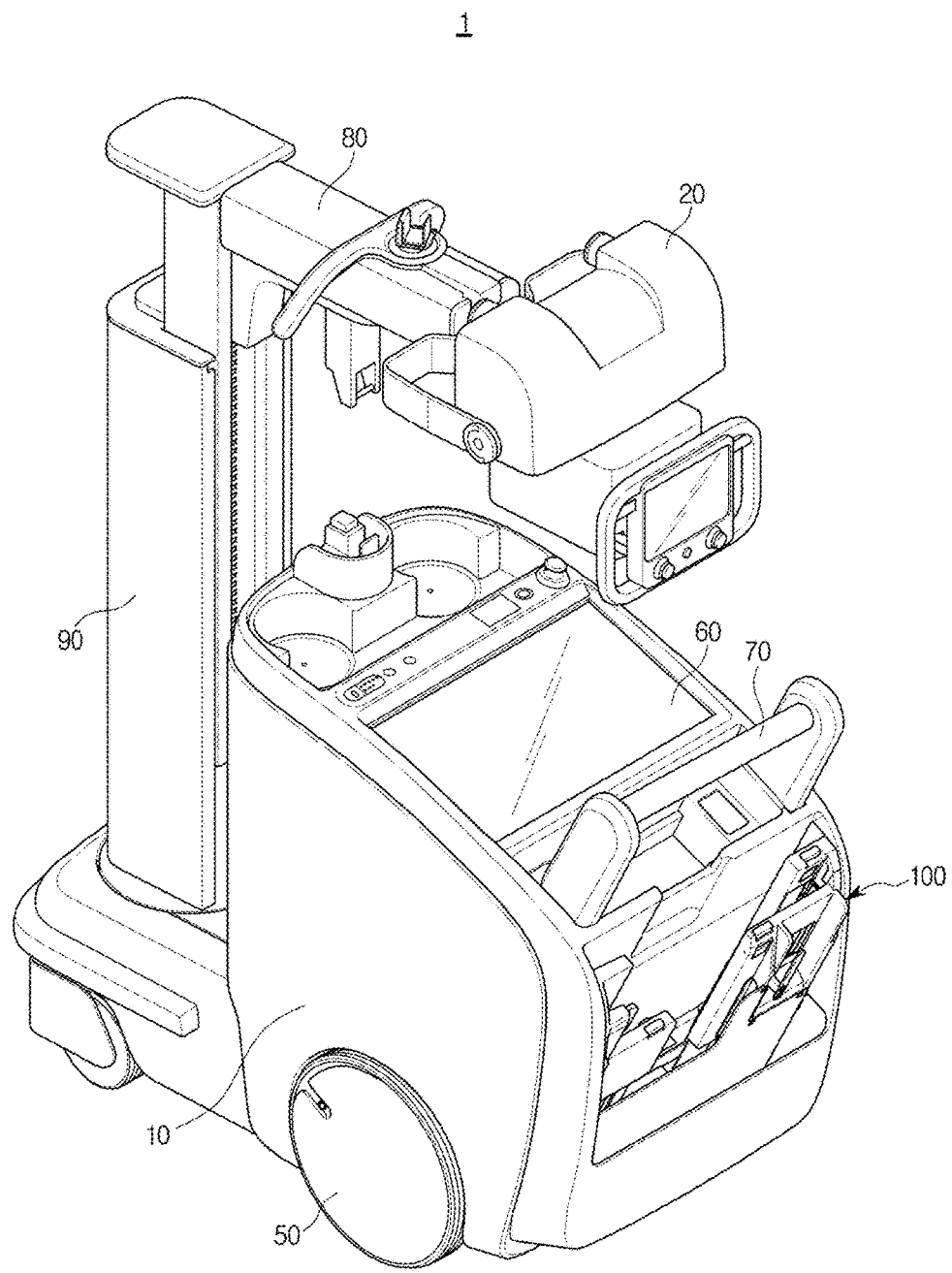
FIG. 1B illustrates a mobile x-ray imaging apparatus according to another embodiment of the present disclosure.

FIG. 1B illustrates a mobile x-ray imaging apparatus according to another embodiment of the present disclosure. Elements using like reference numerals as in FIG. 1A substantially perform the same functions as elements illustrated in FIG. 1A. Since the elements have been described in detail with reference to FIG. 1A, the description of the elements will be omitted to avoid overlapping descriptions.

Figure 2A:
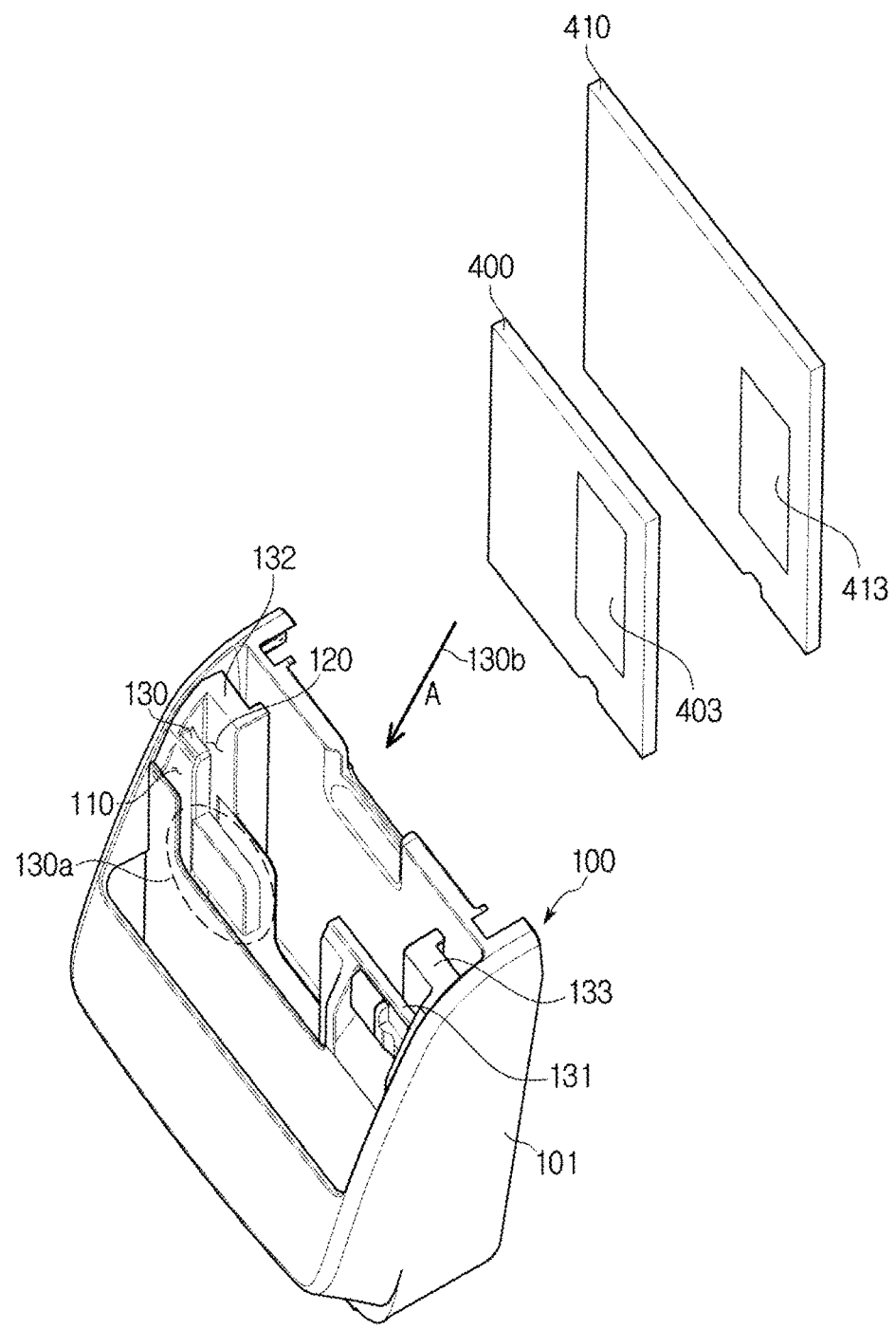
FIG. 2A illustrates a perspective view of a storage unit of a mobile x-ray imaging apparatus and an x-ray detector according to an embodiment of the present disclosure.
Figure 3:
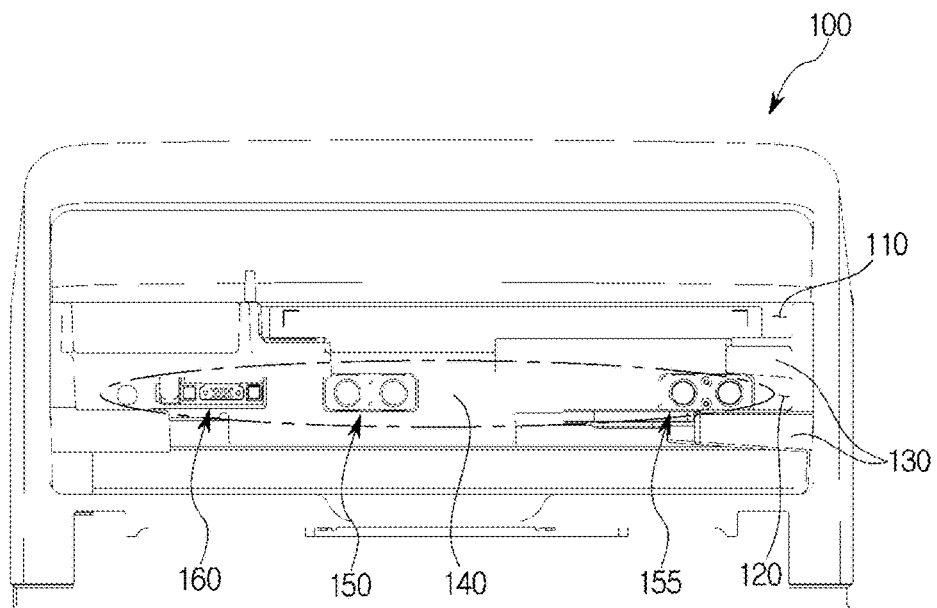
FIG. 3 illustrates a perspective view from a different angle of a storage unit of a mobile x-ray imaging apparatus according to an embodiment of the present disclosure.
Figure 4:
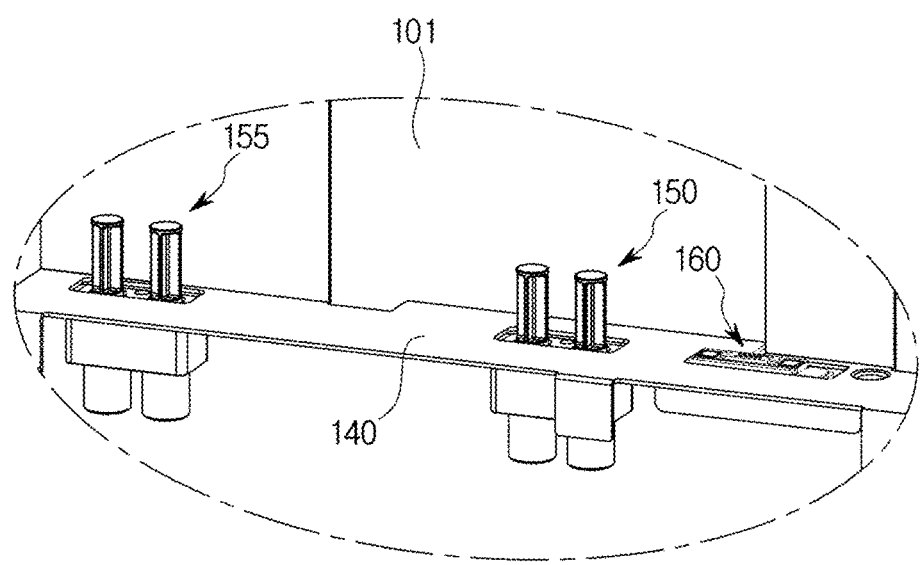
FIG. 4 illustrates a perspective view of a part of the storage unit of FIG. 3.

FIG. 2A illustrates a perspective view of a storage unit of a mobile x-ray imaging apparatus and an x-ray detector according to an embodiment of the present disclosure, and FIG. 3 illustrates a perspective view from a different angle of a storage unit of a mobile x-ray imaging apparatus according to an embodiment of the present disclosure. FIG. 4 illustrates a perspective view illustrating a part of the storage unit of FIG. 3. Specifically, FIG. 4 is a view illustrating a base plate 140 of each of the one or more slots 110 and 120. FIG. 3 is a view of the storage unit 100 from the top.

As illustrated in FIG. 2A to 4, the storage unit 100 may include a body 101 configured to form an exterior of the storage unit 100.

The storage unit 100 may further include the one or more slots 110 and 120 in which the one or more x-ray detectors 30 may be stored.

Sizes of the one or more slots 110 and 120 may be different from each other. The sizes of the one or more slots 110 and 120 are determined according to sizes of the one or more x-ray detectors 30 stored in the one or more slots 110 and 120. For example, the one or more slots 110 and 120 may include a first slot 110 configured to store an x-ray detector having a relatively small size and a second slot 120 configured to store an x-ray detector having a relatively large size. However, sizes of the one or more slots 110 and 120 are not limited to being different from each other and may be modified in various ways. For example, sizes of the one or more slots 110 and 120 may be the same. Also, the number of the one or more slots 110 and 120 is not limited to two.

The storage unit 100 may further include partitions 130, 131, 132, and 133 configured to divide the one or more slots 110 and 120. When described in another manner, when the storage unit 100 includes the plurality of slots 110 and 120, the plurality of slots 110 and 120 may face each other with the partitions 130, 131, 132, and 133 placed therebetween. For example, the first slot 110 and the second slot 120 may face each other with the partitions 130 and 131 placed therebetween. The partitions 130 and 131 may be formed to extend from a sidewall of the body 101 toward the inside of the storage unit 100.

The storage unit 100 may further include the base plate 140 configured to define the one or more slots 110 and 120 with the partitions 130, 131, 132, and 133. Specifically, the one or more slots 110 and 120 may be defined by sidewalls of the body 101, the partitions 130, 131, 132, 133, and the base plate 140.

Meanwhile, a first-sized x-ray detector 400 or a second-sized x-ray detector 410, each having a size different from that of the other, may be stored in the second slot 120.

The first-sized x-ray detector 400 may include a battery 403 therein. According to an embodiment, the first-sized x-ray detector 400 may further include a wireless power receiver in an area in which the battery 403 is arranged.

The second-sized x-ray detector 410 may include a battery 413 therein. According to an embodiment, the second-sized x-ray detector 410 may further include a wireless power receiver in an area in which the battery 413 is arranged.

As illustrated in FIG. 4, the storage unit 100 may further include one or more damping units 150 and 155. The one or more damping units 150 and 155 serve to absorb an impact that may be applied to the one or more x-ray detectors 30 during a process of storing the one or more x-ray detectors 30 in the storage unit 100. The one or more damping units 150 and 155 may be installed at the base plate 140. Gravity acts on the one or more x-ray detectors 30 when the one or more x-ray detectors 30 are being inserted into the one or more slots 110 and 120. Due to gravity, a speed at which the one or more x-ray detectors 30 are inserted into the one or more slots 110 and 120 is increased in a direction I (see FIG. 7B) in which the one or more x-ray detectors 30 are inserted. Accordingly, the one or more x-ray detectors 30 may collide with great force with an inner wall of each of the one or more slots 110 and 120, in particular, the base plate 140 of each of the one or more slots 110 and 120, during a process of storing the one or more x-ray detectors 30 in the one or more slots 110 and 120. The collision between the one or more x-ray detectors 30 and the base plate 140 of each of the one or more slots 110 and 120 may cause breakage of or damage to the one or more x-ray detectors 30. Particularly, serious breakage of or damage to the terminal 31 formed at one side of each of the one or more x-ray detectors 30 and a connector 160 that will be described below may occur. An impact-absorbing member such as rubber, urethane, and silicone may be arranged on the base plate 140 of each of the one or more slots 110 and 120 to absorb an impact applied to the one or more x-ray detectors 30 during the process of storing the one or more x-ray detectors 30 in the one or more slots 110 and 120. However, arranging only the impact-absorbing member is insufficient for absorbing an impact applied to the one or more x-ray detectors 30. Also, only arranging the above impact-absorbing member cannot prevent the speed at which the one or more x-ray detectors 30 are inserted into the one or more slots 110 and 120 from increasing in the direction I (see FIG. 7B) in which the one or more x-ray detectors 30 are inserted. Thus, it is difficult to expect that the one or more x-ray detectors 30 would be accurately docked to the connector 160. That is, because the one or more x-ray detectors 30 are docked to the connector 160 by magnetic force, and gravity acting between the one or more x-ray detectors 30 and the connector 160 is larger than the magnetic force therebetween when the speed at which the one or more x-ray detectors 30 are inserted into the one or more slots 110 and 120 is extremely high, it is difficult to expect that the terminal of each of the one or more x-ray detectors 30 would be accurately coupled to the connector 160.

To solve the above problem, the one or more damping units 150 and 155 may be provided in the storage unit 100. The one or more damping units 150 and 155 may absorb an impact that may be applied to the one or more x-ray detectors 30 during a process of storing the one or more x-ray detectors 30 in the one or more slots 110 and 120 as well as prevent the speed at which the one or more x-ray detectors 30 are inserted into the one or more slots 110 and 120 from increasing in the direction I (see FIG. 7B) in which the one or more x-ray detectors 30 are inserted and improve success rate of docking the one or more x-ray detectors 30 to the connector 160.

The one or more damping unit 150 and 155 may include an air damper, a hydraulic damper, a gas damper, and the like.

The structure of the one or more damping units 150 and 155 will be described in detail below.

As illustrated in FIG. 4, the storage unit 100 may further include the connector 160. The connector 160 may be arranged in the storage unit 100 to be coupled to the terminal 31 formed at one side of each of the one or more x-ray detectors 30. In other words, the connector 160 may be arranged at the base plate 140 of the one or more slots 110 and 120 so that the terminal formed at one side of each of the x-ray detectors can be docked to the connector 160.

The one or more x-ray detectors 30 may be charged, while being stored in the one or more slots 110 and 120, by the terminal 31 of each of the one or more x-ray detectors 30 docked to the connector 160. Also, the one or more x-ray detectors 30 may transmit and receive an electrical signal to and from the controller (not illustrated), by the terminal 31 of each of the one or more x-ray detectors 30 docked to the connector 160.

The connector 160 may include a connector terminal 161 coupled to the terminal 31 of each of the x-ray detectors 30. Also, the connector 160 may further include a connector magnetic body 162 configured to interact with the detector magnetic body 32 provided in each of the one or more x-ray detectors 30. The connector magnetic body 162 may be provided to abut the connector terminal 161. Specifically, the connector magnetic body 162 may be provided at both sides of the connector terminal 161.

The connector 160 may be arranged at the base plate 140 of each of the one or more slots 110 and 120 so that the connector terminal 161 and the connector magnetic body 162 are exposed toward the inside of each of the one or more slots 110 and 120.

The arrangement structure of the connector 160 will be described in detail below.

Figure 2B:
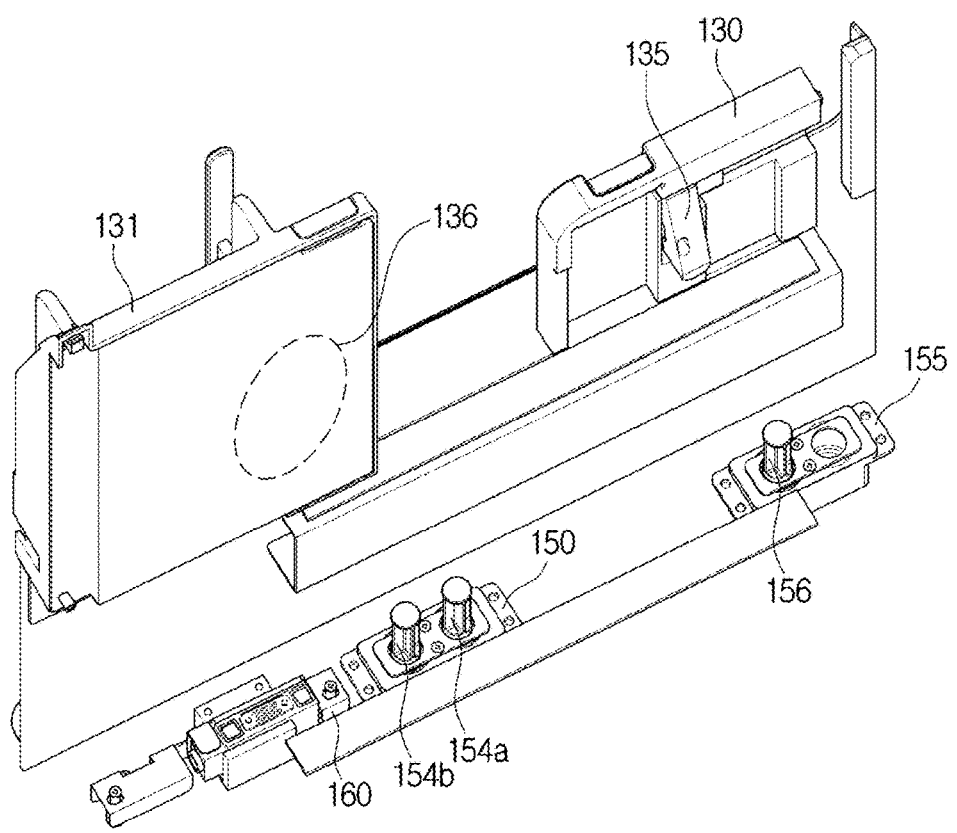
FIG. 2B illustrates a perspective view from a different angle of a storage unit of a mobile x-ray imaging apparatus according to an embodiment of the present disclosure.

FIG. 2B illustrates a perspective view from a different angle of a storage unit of a mobile x-ray imaging apparatus according to an embodiment of the present disclosure.

Referring to FIG. 2B, the partition 130, the partition 131, a guide member 135, a first damping unit 150, a second damping unit 155, and the connector 160 are illustrated.

The guide member 135 may be installed at a rear surface of the partition 130. The guide member 135 may guide the first-sized x-ray detector 400 (see FIG. 2A) having a relatively small size, when the first-sized x-ray detector 400 is being inserted into the second slot 120. Operation of the guide member will be described in detail below with reference to FIG. 2C.

A wireless power transmitter 136 may be placed in the partition 131. The wireless power transmitter 136 may include a coil for power transmission. When the first-sized x-ray detector 400 and the second-sized x-ray detector 410 are stored in the second slot 120 (see FIG. 2A), a wireless power receiver (not illustrated) of each of the first-sized x-ray detector 400 and the second-sized x-ray detector 410 may be placed in an area of each of the first-sized x-ray detector 400 and the second-sized x-ray detector 410 facing the wireless power transmitter 136. Specifically, each of the first-sized x-ray detector 400 and the second-sized x-ray detector 410 may include the wireless power receiver (not illustrated). When each of the first-sized x-ray detector 400 and the second-sized x-ray detector 410 are inserted into the slot, each of the first-sized x-ray detector 400 and the second-sized x-ray detector 410 may receive wireless power transmitted from the wireless power transmitter 136 placed in the partition 131, and a battery (not illustrated) of each of the first-sized x-ray detector 400 and the second-sized x-ray detector 410 may be charged.

The first damping unit 150 may include two dampers 154a and 154b, but embodiments are not limited thereto, and may include a single damper or more than two dampers.

The first damping unit 150 may absorb impact of dropping each of the first-sized x-ray detector 400 having a relatively small size and the second-sized x-ray detector 410 having a relatively large size.

The second damping unit 155 may include a single damper 156, but embodiments are not limited thereto and may also include two or more dampers. The second damping unit 155 may absorb impact of dropping the second-sized x-ray detector.

Figure 2C:
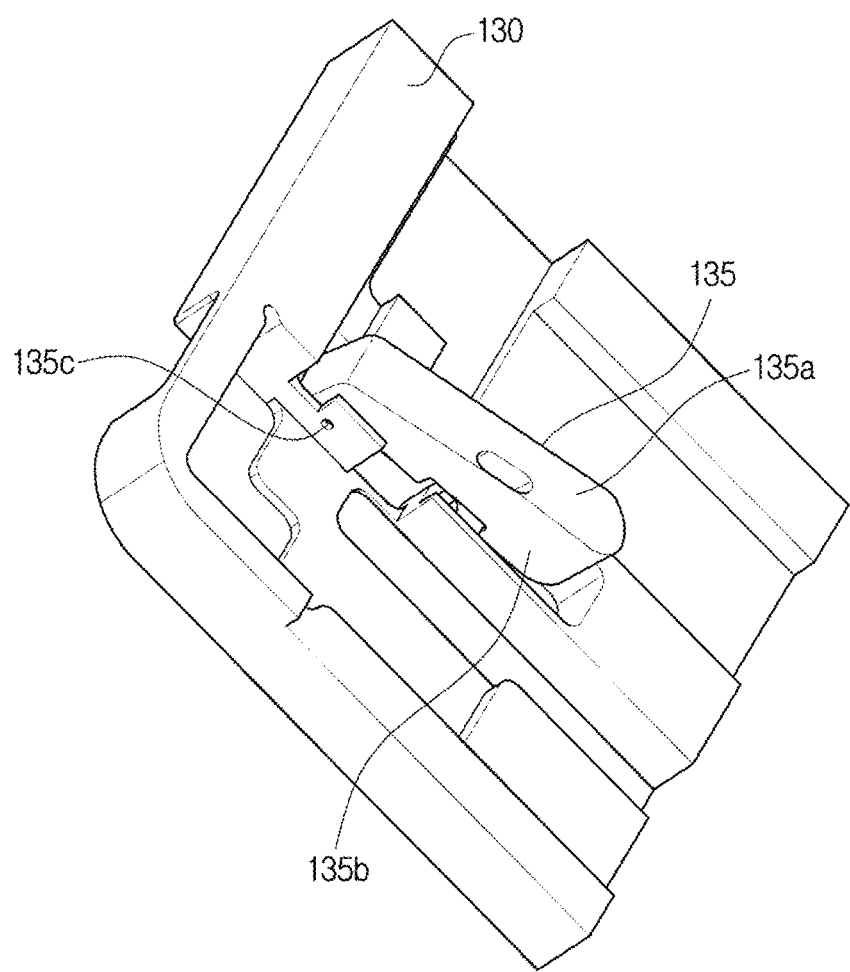
FIG. 2C illustrates an enlarged view of a part of a storage unit of a mobile x-ray imaging apparatus according to an embodiment of the present disclosure.

FIG. 2C illustrates a dotted portion 130a of FIG. 2A viewed along direction A (130b).

Referring to FIG. 2C, the partition 130 and the guide member 135 are illustrated. The guide member 135 may include an upper surface 135a and a side surface 135b. One side of the guide member 135 may be fixed to the partition 130 by a pin 135c and may pivot about the pin 135c as the axis of rotation. The guide member 135 may be stored in the partition 130 or protrude to the outside thereof while pivoting about the pin 135c.

The side surface 135b of the guide member 135 may be exposed to the outside of the partition 130 when the guide member protrudes to the outside of the partition 130. The guide member 135 may further include a spring (not illustrated) therein and may remain protruded to the outside by the spring.

When storing the first-sized x-ray detector 400 (see FIG. 2A) in the second slot 120 (see FIG. 2A), the guide member 135 may remain protruded to the outside of the partition 130 and guide storage of the first-sized x-ray detector 400 (see FIG. 2A). Specifically, the first-sized x-ray detector 400 (see FIG. 2A) may be stored in the second slot 120 as one side of the first-sized x-ray detector 400 (see FIG. 2A) moves along the side surface 135b of the guide member.

When storing the second-sized x-ray detector 410 (see FIG. 2A) in the second slot 120, the second-sized x-ray detector 410 may move along the upper surface 135a of the guide member 135 and be stored in the second slot 120. The second-sized x-ray detector 410 may press the guide member 135 while being inserted into the second slot 120, and the guide member 135 may be stored in the partition 130.

That is, the guide member 135 may protrude to the outside of the partition 130 when the first-sized x-ray detector 400 is inserted into the second slot 120 and may be stored in the partition 130 when the second-sized x-ray detector 410 is inserted into the second slot 120.

Figure 2D:
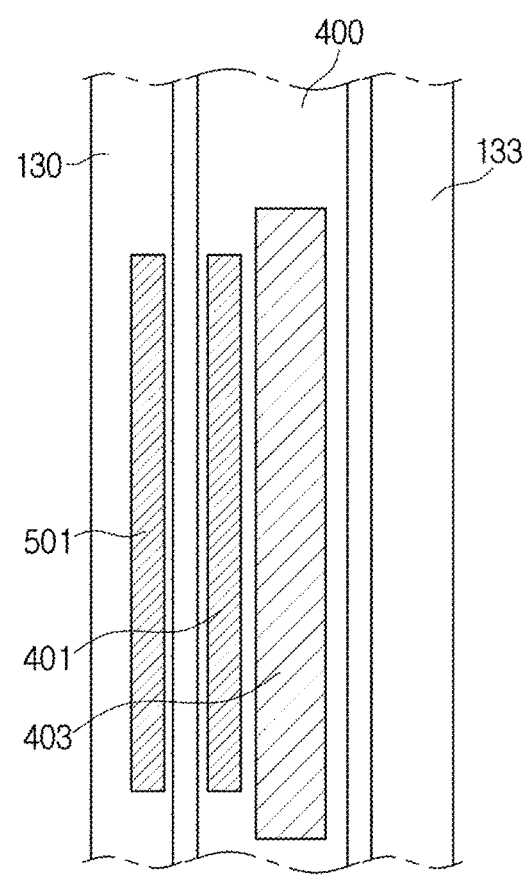
FIG. 2D illustrates a cross-sectional view of a storage unit of a mobile x-ray imaging apparatus according to an embodiment of the present disclosure.

FIG. 2D illustrates a cross-sectional view of a storage unit of a mobile x-ray imaging apparatus according to an embodiment of the present disclosure.

Referring to FIG. 2D, the partitions 130 and 133 and the first-sized x-ray detector 400 are illustrated.

A wireless power transmitter 501 may be arranged in the partition 130.

A wireless power receiver 401 and the battery 403 may be arranged in the first-sized x-ray detector 400. Although the battery 403 is arranged to be parallel to the wireless power receiver 401 according to the embodiment of the present disclosure, embodiments are not necessarily limited thereto, and a location of the battery may be changed depending on arrangement of devices.

The wireless power receiver 401 may be arranged to face the wireless power transmitter 501 when the first-sized x-ray detector is completely docked at a slot. Accordingly, the wireless power receiver 401 may receive wireless power with high efficiency.

Figure 5:
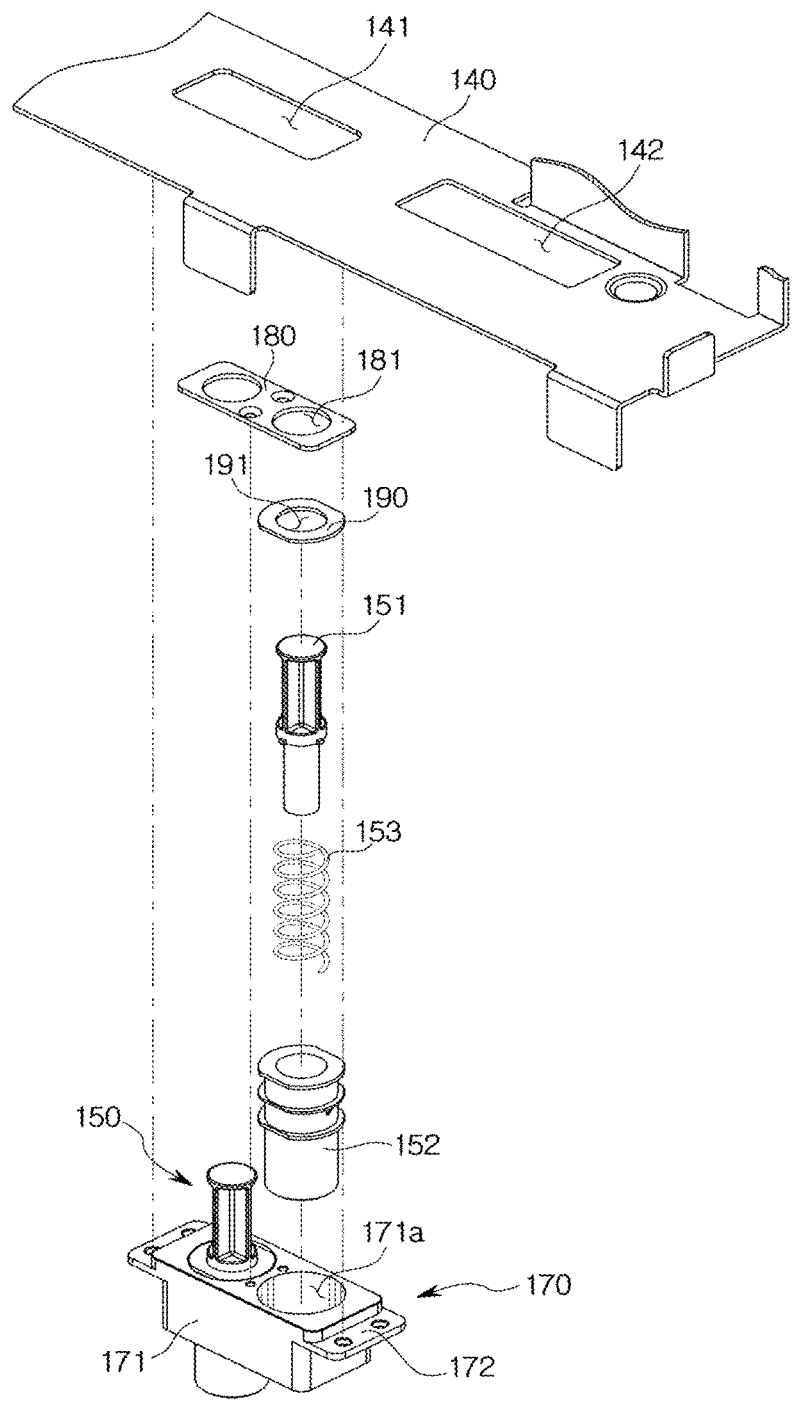
FIG. 5 illustrates an exploded perspective view of a damping unit of a mobile x-ray imaging apparatus according to an embodiment of the present disclosure.

FIG. 5 illustrates an exploded perspective view illustrating a damping unit of a mobile x-ray imaging apparatus according to an embodiment of the present disclosure.

As illustrated in FIG. 5, the first damping unit 150 may be installed at the base plate 140 of the one or more slots 110 and 120 (see FIG. 2A). Although a description is mainly given of the first damping unit 150 below, the description below is also applicable to the second damping unit 155 (see FIG. 4).

The first damping unit 150 may include a piston rod 151.

The first damping unit 150 may further include a cylinder 152 configured to accommodate air compressed or expanded by movement of the piston rod 151.

The first damping unit 150 may further include a spring 153 configured to be elastically deformed according to movement of the piston rod 151.

The first damping unit 150 may further include a lubricant (not illustrated) configured to be accommodated in the cylinder 152 to prevent friction between the cylinder 152 and the piston rod 151.

The storage unit 100 (see FIG. 2A) may further include a fixing member 170 configured to fix and couple the first damping unit 150 to the base plate 140 of the one or more slots 110 and 120.

The fixing member 170 may include a fixing body 171 at which a fixing hole 171a is formed and a fixing rib 172 configured to extend from the fixing body 171. The fixing member 170 may be fixed and coupled to the base plate 140 of the one or more slots by a screw and the like that passes through the fixing rib 172.

A damping unit installation portion 141 may be formed at the base plate 140 of the one or more slots 110 and 120. The damping unit installation portion 141 may have a shape of a hole. The first damping unit 150 may be installed at the base plate 140 of the one or more slots 110 and 120 so that a part of the piston rod 151 protrudes toward the inside of the one or more slots 110 and 120 through the damping unit installation portion 141.

The storage unit 100 may further include a bracket 180 having a damping unit coupling hole 181 to which the first damping unit 150 is coupled. The bracket 180 may be fixed and coupled to the fixing member 170. Specifically, the bracket 180 serves to prevent the piston rod 151 of the first damping unit 150 from being detached.

The storage unit 100 may further include a mounting member 190 arranged between the bracket 180 and the fixing member 170 to prevent, with the bracket 180, the piston rod 151 of the first damping unit 150 from being detached. The mounting member 190 may include a through-hole 191 through which the first damping unit 150 passes.

The fixing member 170 fixes the first damping unit 150 on the outside of the base plate 140 of the one or more slots 110 and 120. The first damping unit 150 is inserted into the damping unit installation portion 141 so that the piston rod 151 faces the inside of the one or more slots 110 and 120 and the cylinder 152 faces the outside of the one or more slots 110 and 120. Here, the cylinder 152 of the first damping unit 150 may be coupled to the fixing hole 171a of the fixing body 171, and the piston rod 151 of the first damping unit 150 may be coupled to the damping unit coupling hole 181 of the bracket 180 and the through-hole 191 of the mounting member 190.

The plurality of damping units 150 and 155 may be installed at the base plate 140 of the one or more slots 110 and 120. The first damping unit 150 may be installed at a central portion of the base plate 140 of the one or more slots 110 and 120, and the second damping unit 155 (see FIG. 4) may be installed at an edge portion of the base plate 140 of the one or more slots 110 and 120.

The first damping unit 150 installed at the central portion of the base plate 140 of the one or more slots 110 and 120 is involved in absorbing an impact on the one or more x-ray detectors 30 stored in the one or more slots 110 and 120. That is, the first damping unit 150 may absorb an impact of dropping the one or more x-ray detectors 30. Here, the one or more x-ray detectors 30 may have any sizes, both large and small, so long as the sizes thereof enable the one or more x-ray detectors 30 to be stored in the one or more slots 110 and 120. In other words, the first damping unit 150 installed at the central portion of the base plate 140 of the one or more slots 110 and 120 may be involved in absorbing an impact on an x-ray detector 30 having a large size as well as in absorbing an impact on an x-ray detector 30 having a small size.

The second damping unit 155 installed at the edge portion of the base plate 140 of the one or more slots 110 and 120 is involved in absorbing an impact on the one or more x-ray detectors 30 stored in the one or more slots 110 and 120. However, here, sizes of the one or more x-ray detectors 30 stored in the one or more slots 110 and 120 may be relatively large. In other words, the second damping unit 155 of the plurality of damping units 150 and 155 may be involved in absorbing an impact on an x-ray detector 30 having a relatively large size.

The number of the one or more damping units 150 and 155 and locations at which the one or more damping units 150 and 155 are arranged may be modified in various ways depending on the size or weight of an x-ray detector 30 for which an impact is to be absorbed.

Figure 6:
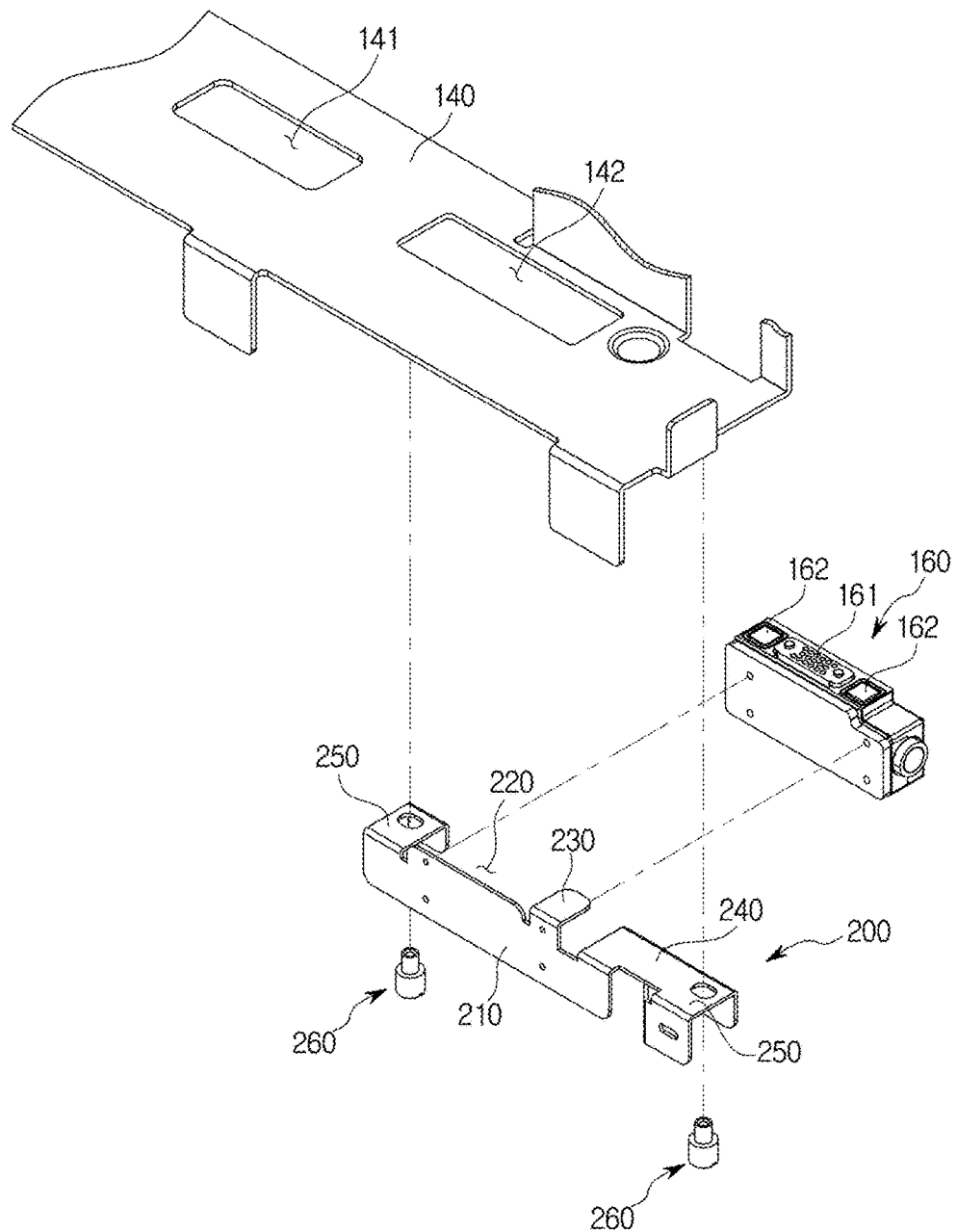
FIG. 6 illustrates a coupling structure of a connector of a mobile x-ray imaging apparatus according to an embodiment of the present disclosure.

FIG. 6 illustrates a coupling structure of a connector of a mobile x-ray imaging apparatus according to an embodiment of the present disclosure.

As illustrated in FIG. 6, the connector 160 may be arranged at the base plate 140 of the one or more slots 110 and 120. A connector installation portion 142 may be formed at the base plate 140 of the one or more slots 110 and 120. The connector installation portion 142 may have a shape of a hole. The connector 160 may be installed at the connector installation portion 142 so that the connector terminal 161 and the connector magnetic body 162 are exposed toward the inside of the one or more slots 110 and 120.

The storage unit 100 may further include a coupling member 200 configured to fix the connector 160 to the base plate 140 of the one or more slots 110 and 120. The coupling member 200 fixes the connector 160 to the base plate 140 of the one or more slots 110 and 120 on the outside of the one or more slots 110 and 120.

A protrusion 143 (see FIG. 8A) may be formed at the base plate 140 of the one or more slots 110 and 120. The protrusion 143 may be formed to protrude to the outside of the base plate 140 of the one or more slots 110 and 120. The protrusion 143 uses the leverage principle and enables the terminal 31 of each of the one or more x-ray detectors 30 to be easily detached from the connector terminal 161. Action of the protrusion 143 will be described in detail below.

The coupling member 200 may include a coupling member body 210.

The coupling member 200 may further include a connector mounting portion 220. The connector mounting portion 220 may have one open surface that faces the base plate 140 of the one or more slots 110 and 120 so that the connector terminal 161 and the connector magnetic body 162 are exposed to the inside of the one or more slots 110 and 120 through the connector installation portion 142. The connector 160 may be fixed and coupled to the coupling member body 210 corresponding to the connector mounting portion 220. Consequently, the connector 160 and the coupling member 200 may move together.

The coupling member 200 may further include a locking portion 230. The locking portion 230 may be bent from the coupling member body 210 toward the rear of the storage unit 100. The locking portion 230 may limit movement of the connector 160 to prevent the connector 160 from moving in a direction opposite to the direction I (see FIG. 7B) in which the one or more x-ray detectors 30 are inserted, while the connector 160 is coupled to the terminal 31 of each of the one or more x-ray detectors 30.

The coupling member 200 may further include a pressing portion 240. The pressing portion 240 may be bent from the coupling member body 210 toward the rear of the storage unit 100. The pressing portion 240 may face the connector mounting portion 220 with the locking portion 230 therebetween. The pressing portion 240 may be pressed by the protrusion 143 formed to protrude from a lower surface of the base plate 140 of the one or more slots 110 and 120. When the one or more x-ray detectors 30 are withdrawn in the direction opposite to the direction I in which the one or more x-ray detectors 30 are inserted while the terminal 31 of each of the one or more x-ray detectors 30 and the connector terminal 161 are coupled to each other, the connector 160 moves a predetermined distance in the direction opposite to the direction I in which the one or more x-ray detectors 30 are inserted. Here, the coupling member 200 also moves together with the connector 160. The connector 160 may move in the direction apposite to the direction I in which the one or more x-ray detectors 30 are inserted, until the protrusion 143 formed at the base plate 140 of the one or more slots 110 and 120 comes into contact with the pressing portion 240 of the coupling member 200. When the protrusion 143 presses the pressing portion 240 of the coupling member 200, one end portion of the connector terminal 161 may be detached from the terminal 31 of each of the one or more x-ray detectors 30, and the connector terminal 161 and the terminal 31 of each of the one or more x-ray detectors 30 may be more easily detached from each other by the leverage principle. That is, as the one or more x-ray detectors 30 are withdrawn from the second slot 120, a part of the coupling member 200 may come into contact with the protrusion 143 and may be pivoted about the protrusion.

As the coupling member 200 pivots, a portion of the connector (the connector terminal 161) coming in contact with the terminal 31 of each of the one or more x-ray detectors 30 may be spaced apart from the terminal 31 of each of the one or more x-ray detectors 30 by the leverage principle.

The coupling member 200 may further include a fixing portion 250. The coupling member 200 may be fixed and coupled to the base plate 140 of the one or more slots 110 and 120 by a fixer 260 configured to pass through the fixing portion 250 and may move in a direction perpendicular to the base plate 140.

Figure 7A:
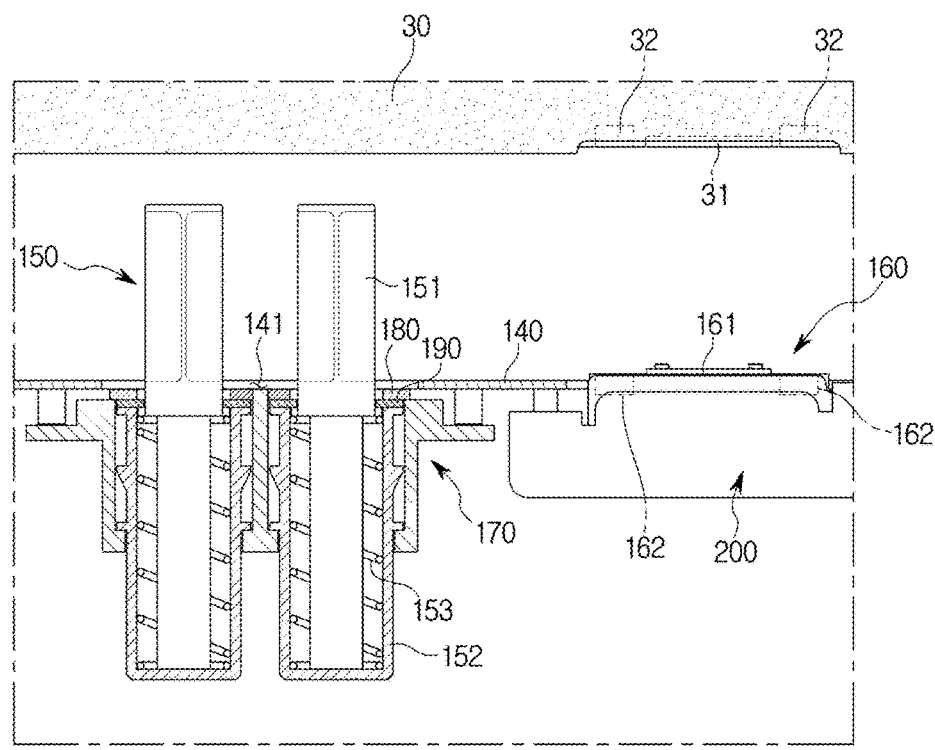
FIGS. 7A to 7C illustrate operational states of a damping unit according to a process of storing an x-ray detector in a storage unit of a mobile x-ray imaging apparatus according to an embodiment of the present disclosure.
Figure 7B:
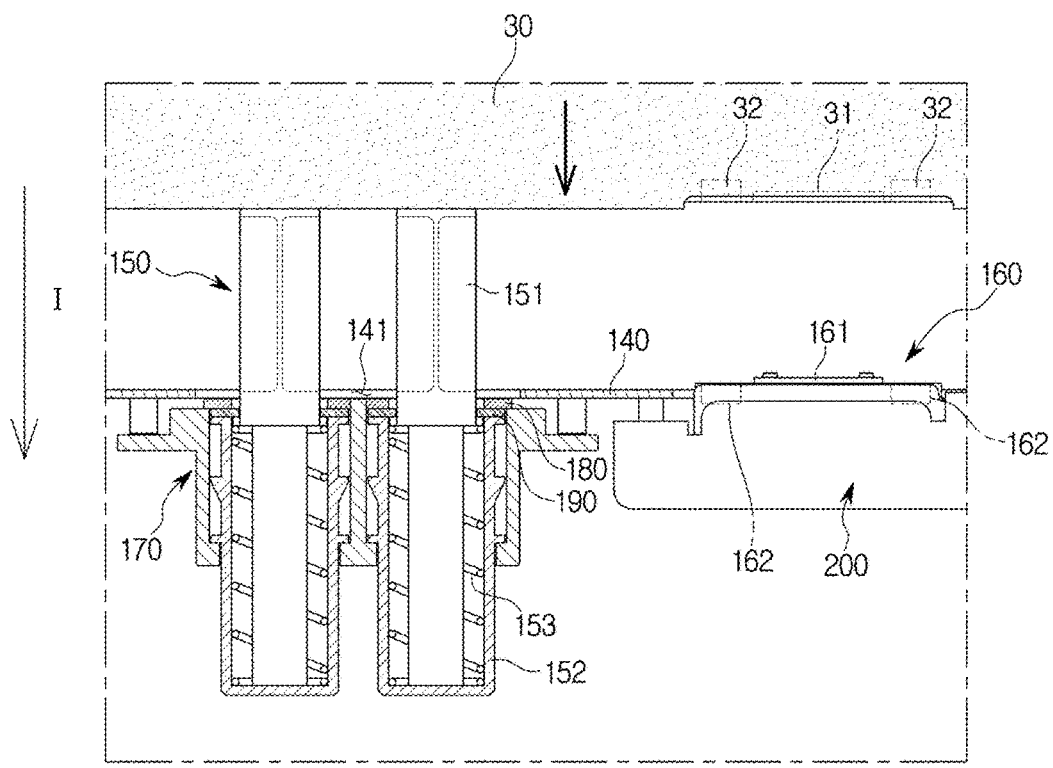
Figure 7C:
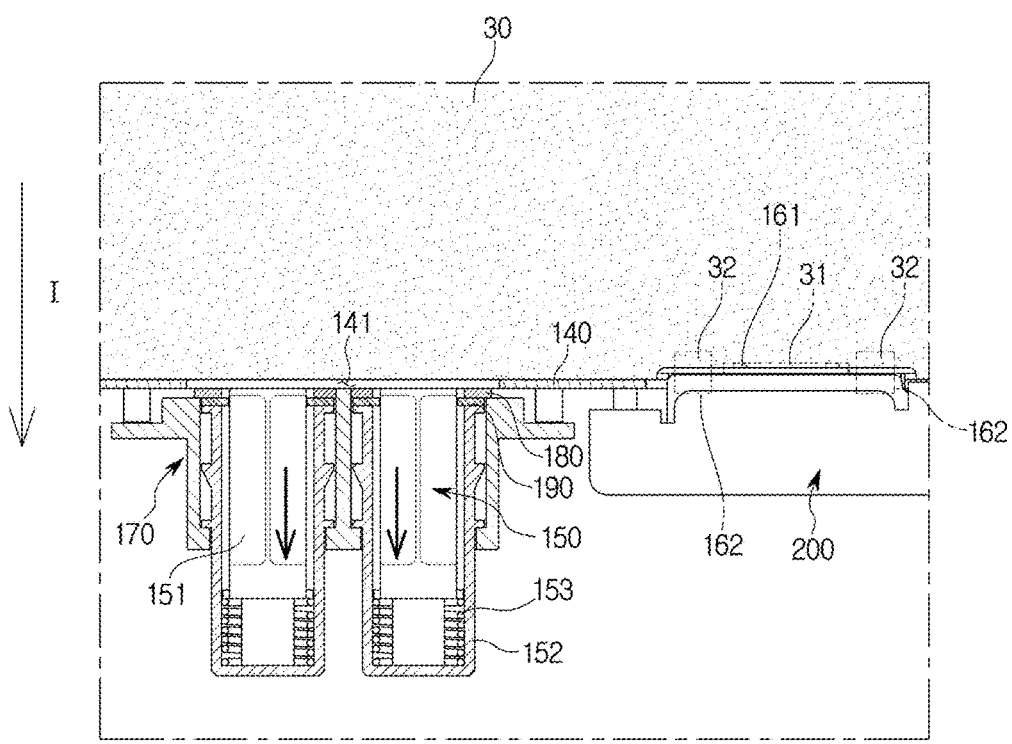

FIGS. 7A to 7C illustrate operational states of a damping unit according to a process of storing an x-ray detector in a storage unit of a mobile x-ray imaging apparatus according to an embodiment of the present disclosure. FIG. 7A illustrates one or more x-ray detectors 30 being inserted into the one or more slots 110 and 120, and FIG. 7B illustrates the one or more x-ray detectors 30 being inserted into the one or more slots 110 and 120 and pressing the first damping unit 150. FIG. 7C illustrates a state in which the first damping unit 150 is pressed by the one or more x-ray detectors 30. FIGS. 7A to 7C are views illustrating a structure of the storage unit 100 viewed from the front.

As illustrated in FIGS. 7A to 7C, the one or more x-ray detectors 30 may be inserted into the one or more slots 110 an 120 so that the terminal 31 of each of the one or more x-ray detectors 30 faces the base plate 140 of the one or more slots 110 and 120. When the one or more x-ray detectors 30 are inserted into the one or more slots 110 and 120, the one or more x-ray detectors 30 are accelerated in the direction I in which the one or more x-ray detectors 30 are inserted due to gravity. Moving speed of the one or more x-ray detectors 30 may be attenuated by the first damping unit 150. In other words, the first damping unit 150 may absorb an impact on the one or more x-ray detectors 30. When the piston rod 151 of the first damping unit 150 is pressed by the one or more x-ray detectors 30, the spring 153 of the first damping unit 150 is contracted in the direction I in which the one or more x-ray detectors 30 are inserted. That is, by the action of the first damping unit 150, acceleration of the one or more x-ray detectors 30 and breakage of or damage to the one or more x-ray detectors 30 due to collision with the base plate 140 of the one or more slots 110 and 120 may be prevented. Also, because acceleration of the one or more x-ray detectors 30 can be prevented by the action of the first damping unit 150, it can be expected that the terminal 31 of each of the one or more x-ray detectors 30 would be accurately docked to the connector terminal 161.

Figure 8A:
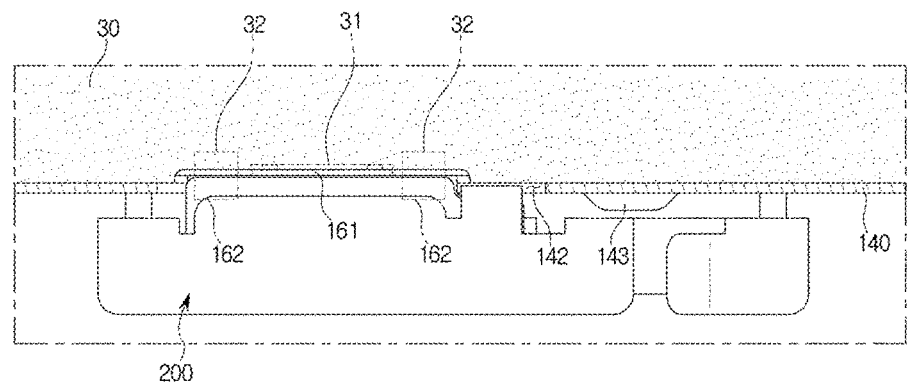
FIGS. 8A to 8D illustrate a process in which an x-ray detector docked to a connector of a mobile x-ray imaging apparatus is released according to an embodiment of the present disclosure.
Figure 8B:
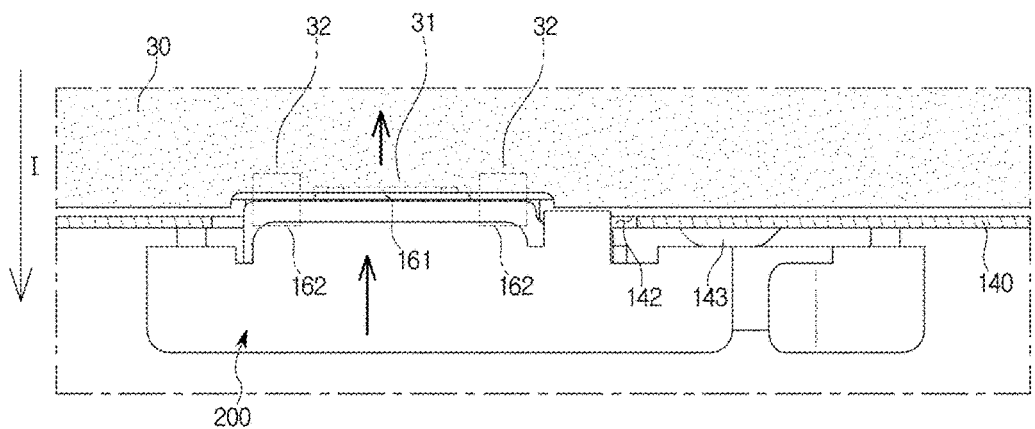
Figure 8C:
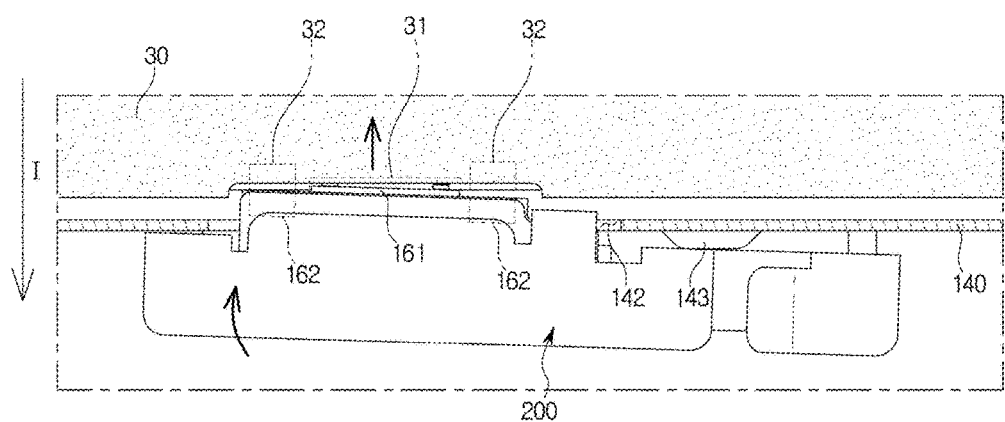
Figure 8D:
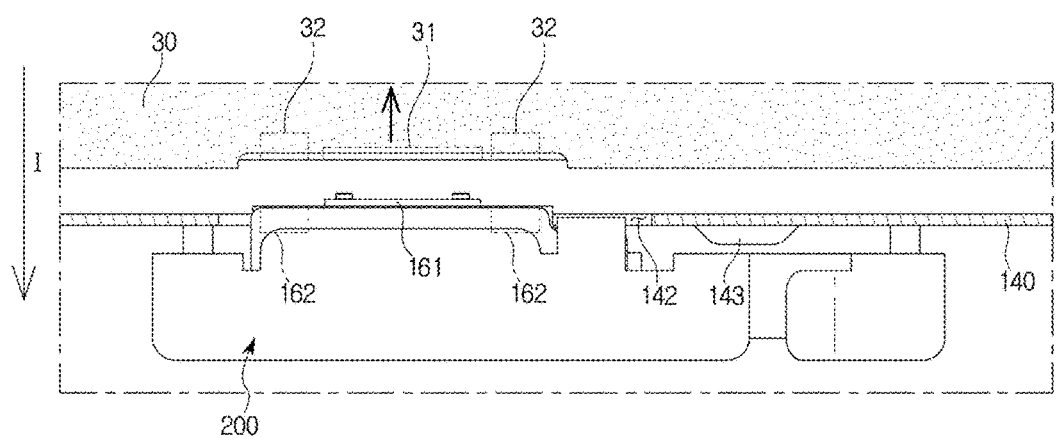

FIGS. 8A to 8D illustrate a process in which an x-ray detector docked to a connector of a mobile x-ray imaging apparatus is released according to an embodiment of the present disclosure. FIG. 8A illustrates a state in which the terminal 31 of each of the one or more x-ray detectors 30 and the connector terminal 161 are coupled by magnetic force and FIG. 8B illustrates a state in which the one or more x-ray detectors 30 and the connector 160 move in the direction opposite to the direction I in which the one or more x-ray detectors 30 are inserted with the terminal 31 of each of the one or more x-ray detectors 30 and the connector terminal 161 coupled to each other. FIG. 8C illustrates a state in which the pressing portion 240 of the coupling member 200 is pressed by the protrusion 143 and one end portion of the connector terminal 161 is detached from the terminal 31 of each of the one or more x-ray detectors 30, and FIG. 8D illustrates a state in which the connector terminal 161 and the terminal 31 of each of the one or more x-ray detectors 30 are completely detached from each other. FIGS. 8A to 8D are views illustrating a structure of the storage unit 100 viewed from the front.

As illustrated in FIGS. 8A to 8D, because the one or more x-ray detectors 30 are gradually inserted into the one or more slots 110 and 120 by the action of the first damping unit 150, the terminal 31 of each of the one or more x-ray detectors 30 and the connector terminal 161 may be docked at accurate positions by magnetic force.

Because the magnetic force acting between the detector magnetic body 32 of each of the one or more x-ray detectors 30 and the connector magnetic body 162 is considerably strong, force larger than the magnetic force acting between the detector magnetic body 32 of each of the one or more x-ray detectors 30 and the connector magnetic body 162 should be applied to withdraw the one or more x-ray detectors 30 from the one or more slots 110 and 120. The leverage principle may be used to reduce such effort.

The connector 160 moves, with the one or more x-ray detectors 30, in the direction opposite to the direction I in which the one or more x-ray detectors 30 are inserted, until the coupling member 200 configured to move together with the connector 160 comes into contact with the protrusion 143. When the protrusion 143 presses the pressing portion 240 of the coupling member 200, one end portion of the connector terminal 161 is detached from the terminal 31 of each of the one or more x-ray detectors 30 by the leverage principle. In this way, the one or more x-ray detectors 30 may be detached from the one or more slots 110 and 120 with small effort.

Figure 9:
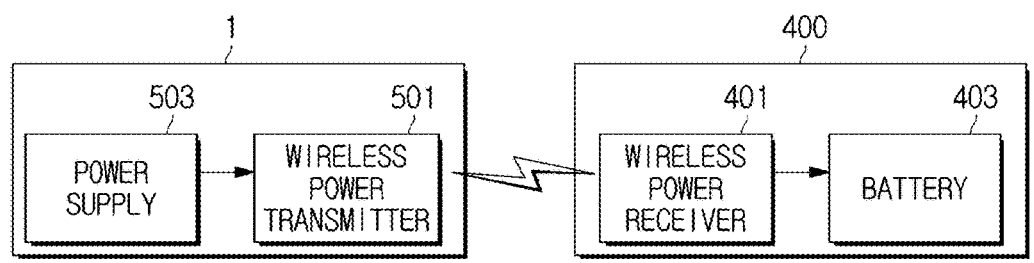
FIG. 9 illustrates an example of wireless power transmission between a mobile x-ray imaging apparatus and an x-ray detector according to an embodiment of the present disclosure.

FIG. 9 illustrates an example of wireless power transmission between a mobile x-ray imaging apparatus and an x-ray detector according to an embodiment of the present disclosure.

Referring to FIG. 9, the mobile x-ray imaging apparatus 1 and the first-sized x-ray detector 400 are illustrated.

The mobile x-ray imaging apparatus 1 may include a power supply 503 and the wireless power transmitter 501.

The power supply 503 receives power from an alternating current (AC) power source or an external power source, converts the received power into a form of power required by the wireless power transmitter 501, and supplies the power to the wireless power transmitter 501.

The wireless power transmitter 501 converts power supplied from a power supply (not illustrated) into wireless power and transmits the wireless power to the first-sized x-ray detector 400. The wireless power transmitted by the wireless power transmitter 501 may be formed in the form of a magnetic field or an electromagnetic wave. For this, the wireless power transmitter 501 may generate wireless power using one or more of a coil, resonator, and an antenna through which wireless power is generated. The wireless power transmitter 501 may include elements configured to generate different forms of wireless power according to different power transmission methods.

For example, the wireless power transmitter 501 may include a primary coil configured to form a magnetic field that changes to induce a current to a secondary coil of the first-sized x-ray detector 400 according to an inductive coupling method. Also, the wireless power transmitter 501 may include a resonator configured to form a magnetic field having a particular resonant frequency to generate a resonance phenomenon in the first-sized x-ray detector 400 according to a resonant inductive coupling method. Also, the wireless power transmitter 501 may include an array antenna that includes a plurality of patch antennas configured to transmit electromagnetic waves having a particular frequency to the first-sized x-ray detector 400 according to an electromagnetic wave method.

Also, the wireless power transmitter 501 may use one or more methods of the inductive coupling method, the resonant inductive coupling method, and the electromagnetic wave method described above to transmit wireless power.

Meanwhile, the wireless power transmitter 501 may further include a circuit configured to adjust features such as frequency, applied voltage, and current used to form wireless power.

The mobile x-ray imaging apparatus 1 may further include a communication unit (not illustrated) according to an embodiment and receive information on a charge state of the battery of the first-sized x-ray detector via the communication unit.

Alternatively, the mobile x-ray imaging apparatus 1 may receive information on the charge state of the battery of the first-sized x-ray detector via a connector that comes into contact with a terminal of the first-sized x-ray detector.

The first-sized x-ray detector 400 may include the wireless power receiver 401 and the battery 403.

The wireless power receiver 401 receives wireless power transmitted from the wireless power transmitter 501. The wireless power receiver 401 may include elements required to receive wireless power according to wireless power transmitting methods. Also, the wireless power receiver 401 may receive wireless power according to one or more wireless power transmitting methods. In such case, the wireless power receiver 401 may simultaneously include elements required for different wireless power transmitting methods.

The wireless power receiver 401 may include one or more of a coil, a resonator, and an antenna configured to receive wireless power transmitted in the form of a magnetic field or an electromagnetic wave.

For example, the wireless power receiver 401 may include, as an element according to an inductive coupling method, a secondary coil through which a current is induced by a changing magnetic field. Also, the wireless power receiver 401 may include, as an element according to a resonant inductive coupling method, a resonant circuit in which a resonance phenomenon occurs by a magnetic field having a particular resonant frequency. Also, the wireless power receiver 401 may include, as an element according to an electromagnetic wave method, an array antenna formed of a plurality of patch antennas configured to receive electromagnetic waves.

The wireless power receiver 401 may further include a rectifier circuit and a regular circuit configured to convert wireless power into a direct current. Also, the wireless power receiver 401 may further include a circuit configured to prevent overvoltage or overcurrent from occurring due to a received power signal.

The first-sized x-ray detector 400 may include a battery.

The first-sized x-ray detector 400 may use wireless power received from the mobile x-ray imaging apparatus 1 to charge the battery and, when the battery is fully charged, transmit charge state information (e.g., charge completion notification data) to the mobile x-ray imaging apparatus 1.

Figure 10:
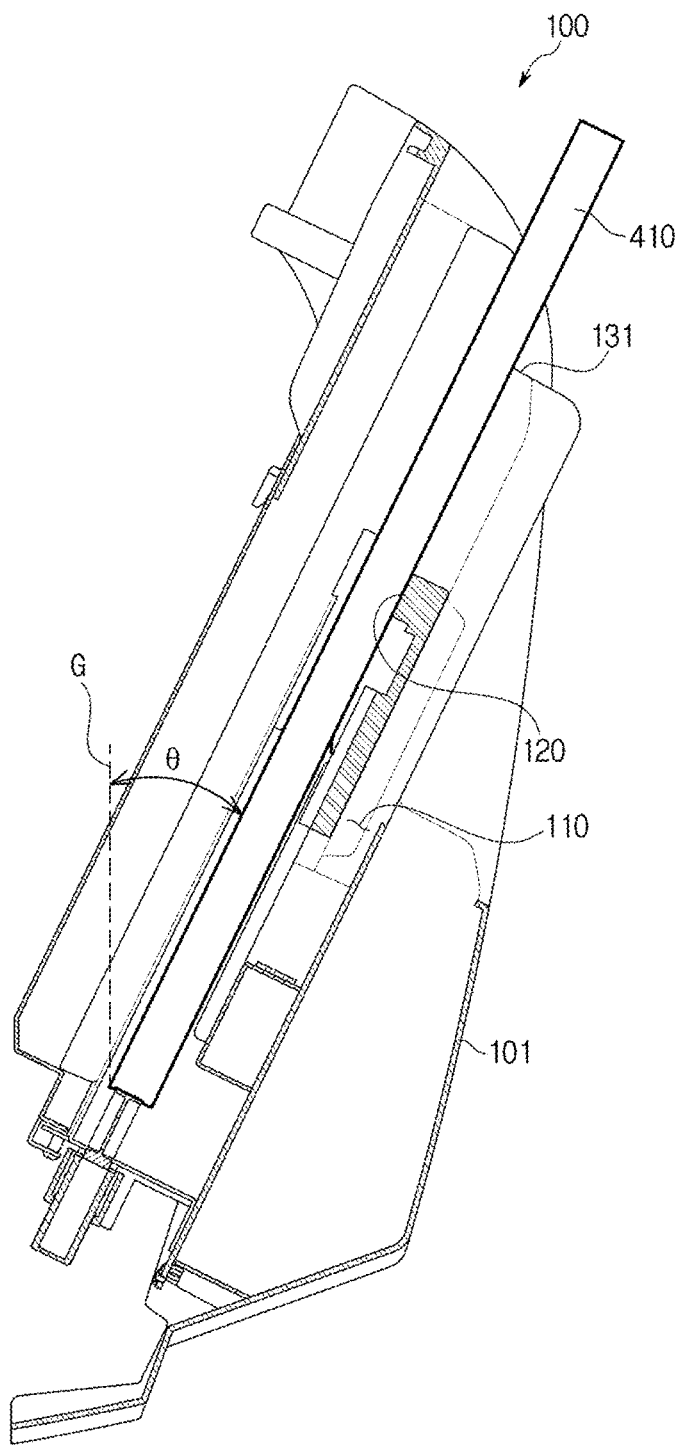
FIG. 10 illustrates a side cross-sectional view of a storage unit of a mobile x-ray imaging apparatus according to an embodiment of the present disclosure.

FIG. 10 illustrates a side cross-sectional view of a storage unit of a mobile x-ray imaging apparatus according to an embodiment of the present disclosure. FIG. 10 illustrates a side cross-sectional view of the storage unit 100 when the second-sized x-ray detector 410 is accommodated in the second slot 120.

As illustrated in FIG. 10, the one or more slots 110 and 120 of the storage unit 100 may be formed at a slant to have a predetermined angle. In other words, the one or more slots 110 and 120 of the storage unit 100 may be inclined to have a predetermined angle with respect to a virtual line G extending in a direction of gravity. Preferably, the one or more slots 110 and 120 of the storage unit 100 may be inclined to have an angle that is larger than 0° and less than or equal to 90° with respect to the virtual line G extending in the direction of gravity. More preferably, the one or more slots 110 and 120 of the storage unit 100 may be inclined to have an angle that is larger than 0° and less than or equal to 45° with respect to the virtual line G extending in the direction of gravity. As an example, FIG. 10 illustrates the second slot 120 of the storage unit 100 formed at a slant to have an angle of about 26° with respect to the virtual line G extending in the direction of gravity. When the one or more slots 110 and 120 of the storage unit 100 are formed to be parallel to the virtual line G extending in the direction of gravity, because the size of gravity acting on the first-sized x-ray detector 400 and the second-sized x-ray detector 410 is relatively large, a relatively large impact may be applied to the first-sized x-ray detector 400 and the second-sized x-ray detector 410 when the first-sized x-ray detector 400 and the second-sized x-ray detector 410 are accommodated in the one or more slots 110 and 120 of the storage unit 100. Conversely, when the one or more slots 110 and 120 of the storage unit 100 are inclined to have an angle of 90° with respect to the virtual line G extending in the direction of gravity, because the size of gravity acting on the first-sized x-ray detector 400 and the second-sized x-ray detector 410 is relatively small, a relatively small impact may be applied to the first-sized x-ray detector 400 and the second-sized x-ray detector 410 when the first-sized x-ray detector 400 and the second-sized x-ray detector 410 are accommodated in the one or more slots 110 and 120 of the storage unit 100. However, when the one or more slots 110 and 120 of the storage unit 100 are inclined to have an angle of 90° with respect to the virtual line G extending in the direction of gravity, a user has to accept inconvenience of having to bend over to store the first-sized x-ray detector 400 and the second-sized x-ray detector 410 into the one or more slots 110 and 120 of the storage unit 100. Consequently, the one or more slots 110 an 120 of the storage unit 100 are preferably inclined to have an angle that is greater than 0° and less than 90° with respect to the virtual line G extending in the direction of gravity. However, because an amount of impact applied to the first-sized x-ray detector 400 and the second-sized x-ray detector 410 can be defined by variables such as a weight of each of the first-sized x-ray detector 400 and the second-sized x-ray detector 410 and a frictional coefficient of each of the first-sized x-ray detector 400 and the second-sized x-ray detector 410, an extent to which the one or more slots 110 and 120 of the storage unit 100 are inclined is not limited to the above examples. For reference, angles of the one or more slots 110 and 120 of the storage unit 100 are measured with respect to one surface of each of the first-sized x-ray detector 400 and the second-sized x-ray detector 410 accommodated in the one or more slots 110 and 120 of the storage unit 100. For example, in the case of FIG. 10, the angle of the second slot 120 is measured with respect to one surface of the second-sized x-ray detector 410 accommodated in the second slot 120, the one surface adjacent to the main body 10 (see FIG. 1B). The angles of the one or more slots 110 and 120 may be equal to each other. That is, the angles of the first slot 110 and the second slot 120 may be equal to each other. However, the angles of the one or more slots 110 and 120 may also be designed to be different from each other.

Since one or more damping units are installed at base plates of one or more slots, x-ray detectors can be prevented from being accelerated in a process of storing the x-ray detectors in the one or more slots.

Since one or more damping units are installed at base plates of one or more slots, an impact that may be applied to x-ray detectors in a process of storing the x-ray detectors in the one or more slots can be minimized.

Since one or more damping units are installed at base plates of one or more slots, x-ray detectors are stored in the one or more slots at an appropriate speed, and success rate of docking between the x-ray detectors and a connector can be improved.

Since a protrusion is formed at base plates of one or more slots, a connector terminal and a terminal of an x-ray detector can be easily detached from each other.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A mobile x-ray imaging apparatus comprising:
 a slot configured to store an x-ray detector;
 a first damping unit installed at a base plate of the slot and configured to absorb an impact on the x-ray detector when the x-ray detector is inserted in the slot;
 a connector installed at the base plate and electrically connected to a terminal of the x-ray detector when the x-ray detector is inserted in the slot; and
 a connector magnetic body installed near the connector, and configured to:
  interact with a detector magnetic body included in the x-ray detector; and
  fix the x-ray detector when the x-ray detector is inserted in the slot,
 wherein the first damping unit protrudes over the base plate and the connector in a direction opposite to an insertion direction of the x-ray detector in the slot, and
 wherein the first damping unit is configured for decelerating the inserted x-ray detector before the inserted x-ray detector contacts the connector.

2. The mobile x-ray imaging apparatus of claim 1, wherein the connector magnetic body is placed at both sides of the connector.

3. The mobile x-ray imaging apparatus of claim 1, further comprising a second damping unit,
 wherein the second damping unit is arranged at an edge of the base plate.

4. The mobile x-ray imaging apparatus of claim 3, wherein the second damping unit is configured to absorb an impact on a second-sized x-ray detector.

5. The mobile x-ray imaging apparatus of claim 1, wherein the first damping unit is configured to absorb an impact on a first-sized x-ray detector and a second-sized x-ray detector.

6. The mobile x-ray imaging apparatus of claim 1, wherein the first damping unit includes two dampers.

7. The mobile x-ray imaging apparatus of claim 6, wherein the first damping unit further includes a bracket configured to support the two dampers.

8. The mobile x-ray imaging apparatus of claim 6, wherein the first damping unit further includes a holder configured to store the two dampers.

9. The mobile x-ray imaging apparatus of claim 1, further comprising a coupling member,
 wherein the coupling member fixes the connector and is connected to the base plate, and
 wherein the coupling member is configured to move in a direction perpendicular to the base plate.

10. The mobile x-ray imaging apparatus of claim 9, wherein a protrusion is formed at a lower surface of the base plate and a part of the coupling member comes into contact with the protrusion when the x-ray detector is withdrawn from the slot, and wherein the coupling member is configured to pivot about the protrusion.

11. The mobile x-ray imaging apparatus of claim 10, wherein, as the coupling member pivots, a portion of the connector that comes into contact with the terminal of the x-ray detector becomes spaced apart from the terminal of the x-ray detector.

12. The mobile x-ray imaging apparatus of claim 1, wherein the first damping unit further includes a piston rod and a cylinder and the cylinder accommodates air compressed by movement of the piston rod.

13. The mobile x-ray imaging apparatus of claim 12, wherein the first damping unit further includes a spring and the spring is elastically deformed according to movement of the piston rod.

14. The mobile x-ray imaging apparatus of claim 1, wherein a partition of the slot includes a guide member and one side of the guide member is configured to pivot about an axis of rotation to be stored in the partition or protrude outside the partition.

15. The mobile x-ray imaging apparatus of claim 14, wherein the guide member includes an upper surface and a side surface and the side surface is exposed to the outside of the partition when the guide member protrudes to the outside of the partition.

16. The mobile x-ray imaging apparatus of claim 15, wherein the upper surface comes into contact with a second-sized x-ray detector when the second-sized x-ray detector is inserted into the slot.

17. The mobile x-ray imaging apparatus of claim 15, wherein the side surface comes into contact with a first-sized x-ray detector when the first-sized x-ray detector is inserted into the slot.

18. The mobile x-ray imaging apparatus of claim 1, wherein a wireless power transmitter is arranged in a partition of the slot and, when the x-ray detector is stored in the slot, the wireless power transmitter transmits wireless power to the x-ray detector.

19. The mobile x-ray imaging apparatus of claim 18, wherein, when the x-ray detector is inserted in the slot, the wireless power transmitter is arranged at a position facing a wireless power receiver of the x-ray detector.

20. A storage unit provided to store an x-ray detector therein, the storage unit comprising:
   a slot configured to store the x-ray detector therein;
   a damping unit installed at a base plate of the slot and configured to absorb an impact on the x-ray detector when the x-ray detector is inserted in the slot;
   a connector installed at the base plate of the slot and electrically connected to a terminal of the x-ray detector when the x-ray detector is inserted in the slot; and
   a connector magnetic body installed adjacent to the connector and configured to:
      interact with a detector magnetic body included in the x-ray detector; and
      fix a position of the x-ray detector when the x-ray detector is inserted in the slot,
   wherein the damping unit protrudes over the base plate and the connector in a direction opposite to an insertion direction of the x-ray detector in the slot, and
   wherein the damping unit is configured for decelerating the inserted x-ray detector before the inserted x-ray detector contacts the connector.

* * * * *